US012702513B2

(12) United States Patent
Campisano et al.

(10) Patent No.: US 12,702,513 B2
(45) Date of Patent: Aug. 11, 2026

(54) SURGEON INPUT SYSTEM USING EVENT-BASED VISION SENSORS FOR A SURGICAL ROBOTIC SYSTEM

(71) Applicant: Asensus Surgical US, Inc., Durham, NC (US)

(72) Inventors: Federico Campisano, Timnath, CO (US); Davide Faconti, Barcelona (ES); Daniel S. Menoher, Hummelstown, PA (US); Somesh Kashyap, Cary, NC (US); Randall L. Luck, Cary, NC (US)

(73) Assignee: KARL STORZ SE & CO. KG, Tuttlingen (DE)

(*) Notice: Subject to any disclaimer, the term of this patent is extended or adjusted under 35 U.S.C. 154(b) by 37 days.

(21) Appl. No.: 18/663,595

(22) Filed: May 14, 2024

(65) Prior Publication Data

US 2024/0382280 A1 Nov. 21, 2024

Related U.S. Application Data

(63) Continuation-in-part of application No. PCT/US2024/016576, filed on Feb. 20, 2024.

(Continued)

(51) Int. Cl.

*A61B 34/00* (2016.01)
*A61B 34/37* (2016.01)
*B25J 13/06* (2006.01)

(52) U.S. Cl.

CPC .............. *A61B 34/74* (2016.02); *A61B 34/37* (2016.02); *B25J 13/06* (2013.01)

(58) Field of Classification Search

CPC .................... A61B 34/74; A61B 34/37; A61B 2017/00203; A61B 2017/00216;

(Continued)

(56) References Cited

U.S. PATENT DOCUMENTS 5,227,985 A 7/1993 DeMenthon
5,388,059 A 2/1995 DeMenthon (Continued)

FOREIGN PATENT DOCUMENTS

WO WO-2015175278 A1 * 11/2015 ............ A61B 34/74
WO 2022185292 A1 9/2022

OTHER PUBLICATIONS

International Search Report and Written opinion of the International Searching Authority dated Jun. 3, 2024 from International Application No. PCT/US2024/016576 filed Feb. 20, 2024.

*Primary Examiner* — Kira Nguyen

(57) ABSTRACT

A user input system for providing input to a robotic surgical system for use in commanding motion of the robotic manipulator utilizes a surgeon input tool configured to be worn or held by a user. The surgeon input tool includes a plurality of LEDs, each emitting at different blink frequency and duty cycle. Event-based cameras disposed around a surgeon console are used to capture user movement of the surgeon input tool. The system receives input from the event cameras in response to sensing of light from the LEDs on the surgeon input tool, and uses that information to estimated position and/or orientation of the surgeon input tool. Motion commands corresponding to desired movement of the surgical instrument by the robotic manipulator arm are generated based on the estimated position or pose.

20 Claims, 10 Drawing Sheets

Related U.S. Application Data

(60) Provisional application No. 63/507,440, filed on Jun. 9, 2023, provisional application No. 63/486,001, filed on Feb. 20, 2023.

(58) Field of Classification Search
CPC .. A61B 2017/00477; A61B 2034/2048; A61B 2034/2055; B25J 13/06; B25J 13/02; G06F 3/0346
USPC .......................................................... 700/264
See application file for complete search history.

(56) References Cited

U.S. PATENT DOCUMENTS

| | | | | |
|---|---|---|---|---|
| 5,876,325 | A | 3/1999 | Mizuno et al. | |
| 8,521,331 | B2 | 8/2013 | Ithowitz | |
| 8,543,240 | B2 | 9/2013 | Ithowitz et al. | |
| 8,682,489 | B2 | 3/2014 | Ithowitz et al. | |
| 8,696,458 | B2 | 4/2014 | Foxlin et al. | |
| 8,812,160 | B2 | 8/2014 | Hagn et al. | |
| 8,831,782 | B2 | 9/2014 | Ithowitz | |
| 8,935,003 | B2 | 1/2015 | Ithowitz et al. | |
| 8,996,173 | B2 | 3/2015 | Ithowitz et al. | |
| 9,743,989 | B2 | 8/2017 | Ithowitz et al. | |
| 9,901,402 | B2 | 2/2018 | Ithowitz et al. | |
| 10,052,164 | B2 | 8/2018 | Overmyer | |
| 10,085,810 | B2 | 10/2018 | Vakharia et al. | |
| 10,383,699 | B2 | 8/2019 | Kilroy et al. | |
| 10,507,063 | B2 | 12/2019 | Zuhars et al. | |
| 10,543,050 | B2 | 1/2020 | Ithowitz et al. | |
| 10,617,484 | B2 | 4/2020 | Kilroy et al. | |
| 10,751,133 | B2 | 8/2020 | Toporek et al. | |
| 10,881,953 | B2 | 1/2021 | Yamano et al. | |
| 11,013,562 | B2 | 5/2021 | Marti et al. | |
| 11,062,465 | B2 | 7/2021 | Stopp et al. | |
| 11,229,487 | B2 | 1/2022 | Zuhars et al. | |
| 11,266,469 | B2 | 3/2022 | Fuerst et al. | |
| 11,291,507 | B2 | 4/2022 | Stawiaski et al. | |
| 11,350,997 | B2 | 6/2022 | Marti et al. | |
| 11,351,001 | B2 | 6/2022 | Jare | |
| 11,395,706 | B2 | 7/2022 | Joshi et al. | |
| 11,534,246 | B2 | 12/2022 | Fuerst et al. | |
| 11,666,401 | B2 | 6/2023 | Denlinger et al. | |
| 11,707,336 | B2 | 7/2023 | Ithowitz et al. | |
| 11,857,285 | B2 | 1/2024 | Kapadia et al. | |
| 2011/0040305 | A1* | 2/2011 | Gomez | A61B 34/74<br>606/130 |
| 2019/0192240 | A1* | 6/2019 | Mintz | B25J 9/0084 |
| 2021/0259779 | A1 | 8/2021 | Fuerst et al. | |
| 2022/0032473 | A1 | 2/2022 | Maret | |
| 2022/0151710 | A1 | 5/2022 | Marti et al. | |
| 2022/0183770 | A1 | 6/2022 | Nikou | |
| 2022/0244566 | A1* | 8/2022 | Fuerst | G06F 3/012 |
| 2022/0361972 | A1 | 11/2022 | Armand et al. | |
| 2023/0346494 | A1 | 11/2023 | Ithowitz et al. | |
| 2024/0148447 | A1* | 5/2024 | Stein | A61B 34/20 |
| 2025/0127577 | A1* | 4/2025 | Loschak | A61B 90/92 |

* cited by examiner

SURGEON INPUT SYSTEM USING EVENT-BASED VISION SENSORS FOR A SURGICAL ROBOTIC SYSTEM

REFERENCE TO RELATED APPLICATIONS

This application is a continuation-in-part of PCT/US24/16576, filed Feb. 20, 2024, which claims the benefit of U.S. Provisional Application No. 63/486,001, filed Feb. 20, 2023, and U.S. Provisional Application No. 63/507,440, filed Jun. 9, 2023.

TECHNICAL FIELD OF THE INVENTION

The present invention relates generally to the field of robot-assisted surgical devices and systems, and more particularly to devices and systems for providing user input to surgical robotic systems to cause corresponding movement of surgical instruments at a surgical site.

BACKGROUND

There are various types of surgical robotic systems on the market or under development. Some surgical robotic systems use a plurality of robotic manipulators or arms. Each manipulator carries a surgical instrument, or the camera (known as a laparoscope or endoscope) used to capture images from within the body for display on a monitor. Typical configurations allow two or three instruments and the camera to be supported and manipulated by the system. Input to the system is generated based on input from a surgeon positioned at a surgeon console, typically using input devices such as input handles. The system responds to movement of a user input device by controlling the robotic manipulator that is associated with that input device to position, orient and actuate the surgical instrument positioned on that manipulator. The image captured by the camera is shown on a display at the surgeon console. The console may be located patient-side, within the sterile field, or outside of the sterile field.

Each robotic manipulator includes a portion, typically at the terminal end of the arm, that is designed to support and operate a surgical device assembly. The surgical device assembly includes a surgical instrument having a shaft, a distal end effector on the shaft, and an adapter at the proximal end of the shaft that facilitates engagement of the instrument with the robotic manipulator. The end effector is positionable within a patient. The end effector may be one of many different types that are used in surgery including, without limitation, end effectors having one or more of the following features: jaws that open and close, a section at the distal end of the shaft that bends or articulates in one or more degrees of freedom, a tip that rolls axially relative to the shaft, a shaft that rolls axially relative to the manipulator arm.

During robot-assisted minimally invasive surgeries, the surgical instruments are inserted into the patient body through a surgical device called a trocar, which is located at the incision site. For patient safety and to prevent injury at the incision site, a motion constraint is placed on lateral translation of the instrument shaft at the location of the trocar. The combination of both motion of the instrument distal-end and constraint at the trocar define the motion pattern for manipulators designed for minimally invasive procedures.

More specifically, each surgical instrument must pivot with respect to a remote center of motion (RCM) at the incision site. Accordingly, motion of the surgical instrument shaft is limited to pitch and yaw motion relative to the RCM, as well as translational motion along the instrument's longitudinal axis, and rotational or "roll" motion relative to the instrument's longitudinal axis. Commercially available surgical robotic systems use different approaches to ensure that instrument motion is constrained relative to the RCM. One approach is to mechanically constrain instrument motion such that it occurs relative to the RCM. In such systems, the mechanical structure of these manipulators constrains them to move the instrument with respect to a fulcrum. Other surgical robotic systems do not use mechanical constraints to restrict instrument motion to an RCM, but instead use algorithms to constrain such motion such that it occurs relative to a fulcrum at the incision.

Robotic surgical systems may offer additional functionality beyond pitch, roll, jaw and insertional movement of the instrument shaft. This may include open and close actuation of jaws of the instrument, articulation or bending of the distal end of the instrument shaft, and/or roll the instrument's distal tip using electromechanical actuation (or hydraulic/pneumatic actuation). The number of degrees of freedom (DOFs) of motion for a robotically controlled instrument can vary between surgical systems and also between the different devices used for a particular system. Likewise, instruments with varying levels of complexity can be used interchangeably on a particular type of robotic system.

The instruments are exchangeable during the course of the procedure, allowing one instrument (with its corresponding adapter) to be removed from a manipulator and replaced with another instrument and its corresponding adapter.

As discussed above, the desired motion of the distal-end of the surgical instrument is commanded by the surgeon through the user inputs. The robotic manipulator on the patient side replicates the motion commanded by the surgeon on the instrument. For some commercially available robotic systems, the user inputs are configured for laparoscopic motion, mimicking the hand motion a surgeon would use when manually maneuvering a laparoscopic instrument. In manual laparoscopic surgery, the instrument shafts pivot about a fulcrum at the incision site. Thus, when the surgeon moves the instrument handle upwardly, the tip of the instrument moves downwardly in the body. Surgical robotic consoles offering laparoscopic motion simulate this motion, providing user interfaces having handles that move and give input in a manner familiar to the surgeons.

Another type of instrument handle motion used in robotic surgery is referred to as "true cartesian motion," which differs from laparoscopic motion in that there is no inversion of the motion. When using a surgeon console offering true cartesian motion, the user input handle is raised to cause the surgical robotic system to raise the instrument tip, moved left to cause movement of the tip to the left, etc. Some surgical systems may allow surgical personnel to choose whether the system will operate in a laparoscopic type of mode or in a true cartesian motion mode.

Optical tracking systems are used in a variety of medical applications. For example, some surgical interventions employ surgical navigation systems that use optical tracking. In such systems, the optical tracking system tracks passive or active tracking elements on the surgical instrument. These types of optical tracking systems make use of two or more cameras that capture images of the tracking elements on the instrument. Triangulation is used to determine the 3D positions of the tracking features in space. In cases where the instrument has multiple tracking elements (ideally 3 or more) in known relative positions, the tracking systems can also determine the 3D orientation of the instrument. In the case of optically tracked surgical instruments, this allows the system to determine the location of the distal tip of a surgical instrument, which can be registered with preoperative planning images and displayed to the user to facilitate navigation of the instrument.

Conventional surgeon consoles have input devices coupled to mechanical linkages or gimbles. More recently, consoles have been proposed in which the user input handles are tracked using electromagnetic tracking, optical tracking or other forms of tracking such as inertial tracking. Regardless of the type of tracking technology used in such systems, performance of the robotic surgical requires that the robotic manipulator replicate the motion of the user input (i.e. to produce the desired instrument end-effector velocity) in real-time, without any lag that would be perceptible to the user.

This application describes a novel form of tracking configuration for use in tracking user input devices at a surgeon console for use in commanding motion of a surgical instrument of a surgical robotic system. The user input system described herein may be used to command any of the types of motion described above, and for some robotic surgical systems it may be configured to allow the user to instruct the system as to which type of motion (e.g. laparoscopic or true cartesian) is to be commanded.

DETAILED DESCRIPTION

Figure 1:
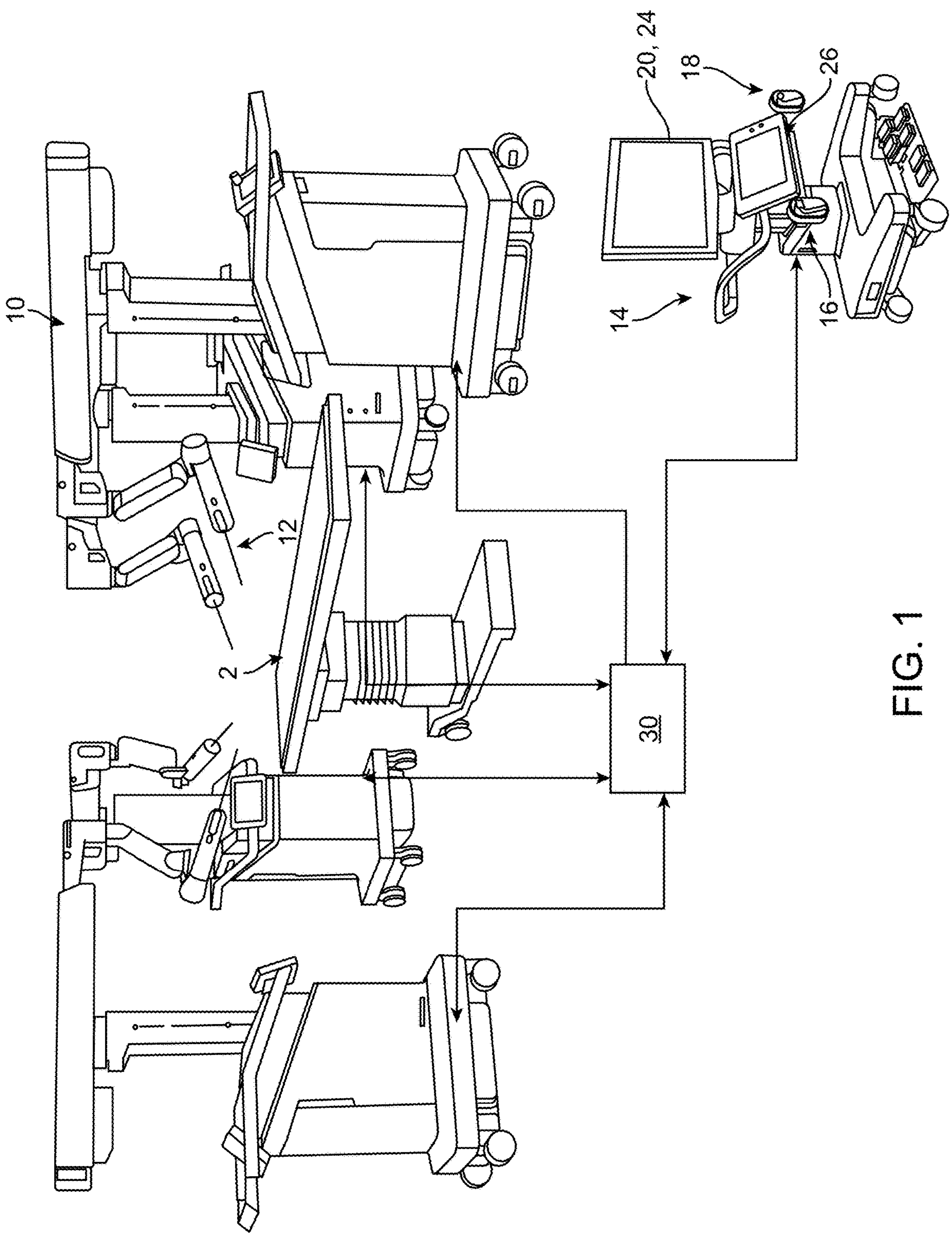
FIG. 1 is a perspective view of a robot-assisted surgical system comprising four robotic manipulator arms of the type described in this application.

The concepts described herein may be used with any robotic surgical system in which a user manipulates user input devices, such as grips or handles, to input desired instrument movement so that the surgical robotic system can generate commands to move and orient the surgical instrument as instructed by the user. By way of example only, the embodiments will be described with reference to the system shown in FIG. 1. In the illustrated system, robotic manipulators 10 are disposed adjacent to a patient bed 2. Each manipulator 10 is configured to maneuver a surgical instrument 12 which has a distal end effector positionable in a patient body cavity. FIG. 1 shows four robotic manipulators, although in other configurations, the number of manipulators may differ.

A surgeon console 14 has two input devices such as handles 16, 18. The input devices are configured to be manipulated by a user to generate signals that are used to command motion of the robotic manipulators in multiple degrees of freedom in order to maneuver the instrument end effectors within the body cavity. As described in greater detail below, the input devices may take the form of handles that are tracked using event sensors, either alone or in combination with inertial tracking sensors such as inertial measurement units on or within the handles.

In use, a user selectively assigns the two handles 16, 18 to two of the robotic manipulators 10, allowing surgeon control of two of the surgical instruments 12 at any given time. To control a third one of the instruments disposed at the working site, one of the two handles 16, 18 may be operatively disengaged from one of the initial two instruments and then operatively paired with the third instrument, or another form of input may control the third instrument as described in the next paragraph.

One of the instruments 12 is a camera that captures images of the operative field in the body cavity. The camera may be moved by its corresponding robotic manipulator using input from a variety of types of input devices, including, without limitation, one of the handles or input tools 16, 18, additional controls on the console, a foot pedal, an eye tracker 20, voice controller, etc. The console may also include a display or monitor 24 configured to display the images captured by the endoscopic/laparoscopic camera, and for optionally displaying system information, patient information, etc. An auxiliary display 26, which may be a touch screen display, can further facilitate interactions with the system.

During use, the surgeon sits or stands at the console 14 while observing the images from the camera that are shown on the display 24, and moves the input tools 16, 18 to generate input to the system that is used to command motion of the instruments 12 by the robotic manipulators 10.

The surgical system allows the operating room staff to remove and replace the surgical instrument 12 on a manipulator 10 based on the surgical need. When an instrument exchange is necessary, surgical personnel remove an instrument from a manipulator arm and replace it with another.

Figure 2:
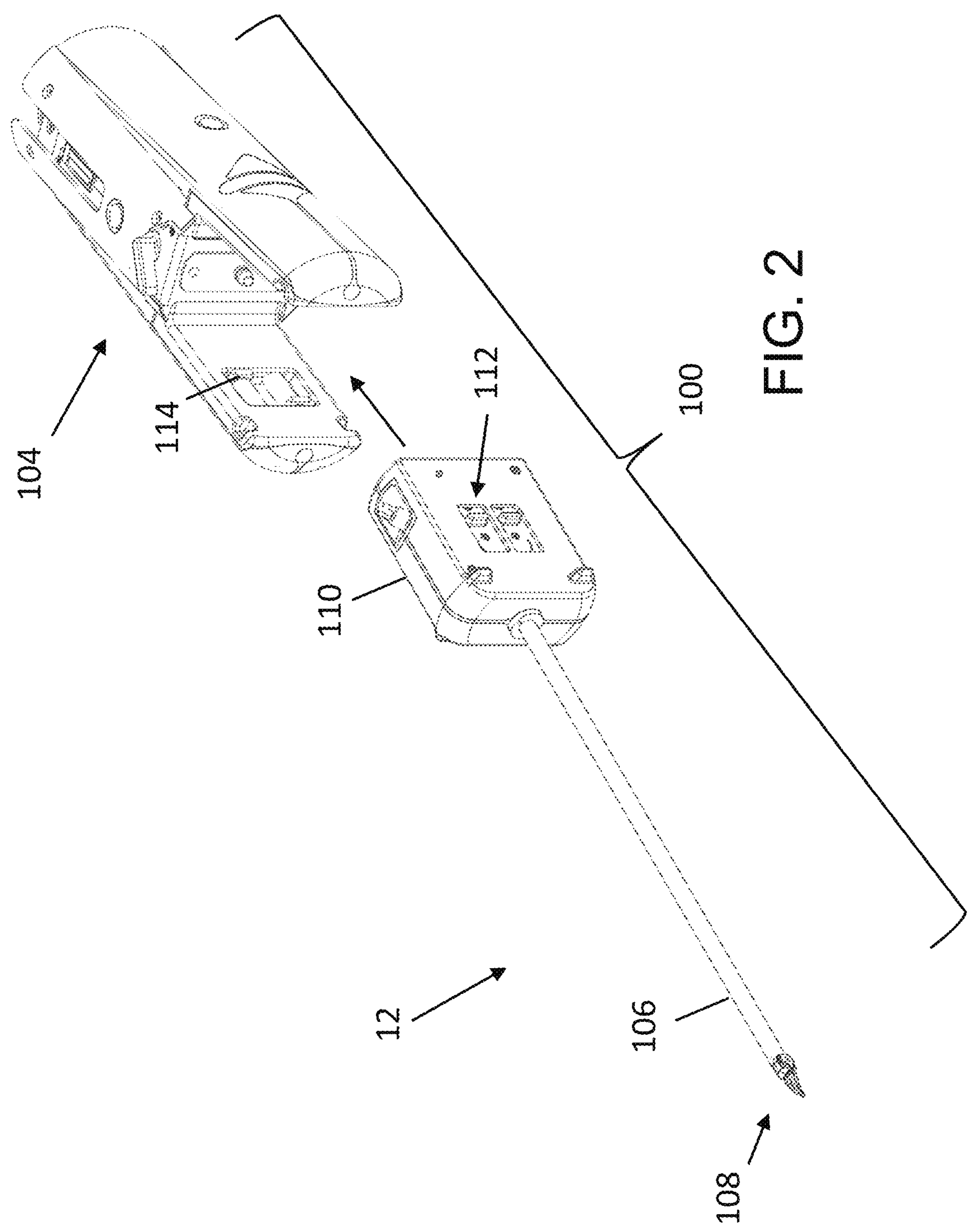
FIG. 2 is a perspective view showing the IDS of FIG. 1 and the surgical instrument separated from the IDS.

Referring to FIGS. 2, positioned at the distal end of each manipulator arm is a receiver 104, which may also be referred to as an instrument drive assembly (IDS). A different surgical instrument 12 is removably mountable to each IDS. Each instrument 12 includes an elongate shaft 106, which is preferably rigid but which may be flexible or partially flexible in alternative systems. An end effector 108 is positioned at the distal end of shaft 106, and a base assembly or adapter assembly 110 is at the proximal end.

Instrument and IDS configurations suitable for use with the disclosed inventions will next be described, but it should be understood that these are given by way of example only. The disclosed user input configuration may be used to generate input for commanding robotic manipulators having various configurations of instruments and instrument drive systems. More particularly, while the IDS described here is configured to drive pitch, yaw and jaw open/close motion of an articulated surgical instrument, in alternative embodiments the IDS may have less functionality. In some alternative configurations, it may serve simply to receive an instrument and to drive jaw open/close operations. In other configurations, it may be configured, along with the instrument, to actuate a roll function of the instrument tip relative to the shaft of the instrument.

The instrument depicted in the drawings is the type described in Applicant's commonly-owned co-pending application published as US 2020/0375680, entitled Articulating Surgical Instrument, which is incorporated herein by reference. The instrument has an elongate shaft with an articulating wrist at its distal end. It makes use of four drive cables two of which terminate at one of the jaw members and the other two of which terminate at the other jaw member. This can be two cables looped at the end effector (so each of the two free ends of each cable loop is at the proximal end) or it can be four individual cables. As described in the co-pending application, the tension on the cables is varied in different combinations to effect articulation of the wrist to cause pitch and yaw motion of the jaw members relative to the instrument shaft, and to cause and jaw open-close functions. Other instruments useful with the system will have other numbers of cables, with the specific number dictated by the instrument functions, the degrees of freedom of the instrument and the specific configuration of the actuation components of the instrument. The surgical instrument's drive cables extend from the end effector 108 through the shaft 106 (FIG. 2) and extend into the adapter assembly 110 where they are coupled to mechanical actuators. A more detailed description is given in Applicant's co-pending application published as US 2021/169595, which is incorporated herein by reference, but a general configuration of these actuators with respect to the adapter assembly will be provided here.

Figure 3:
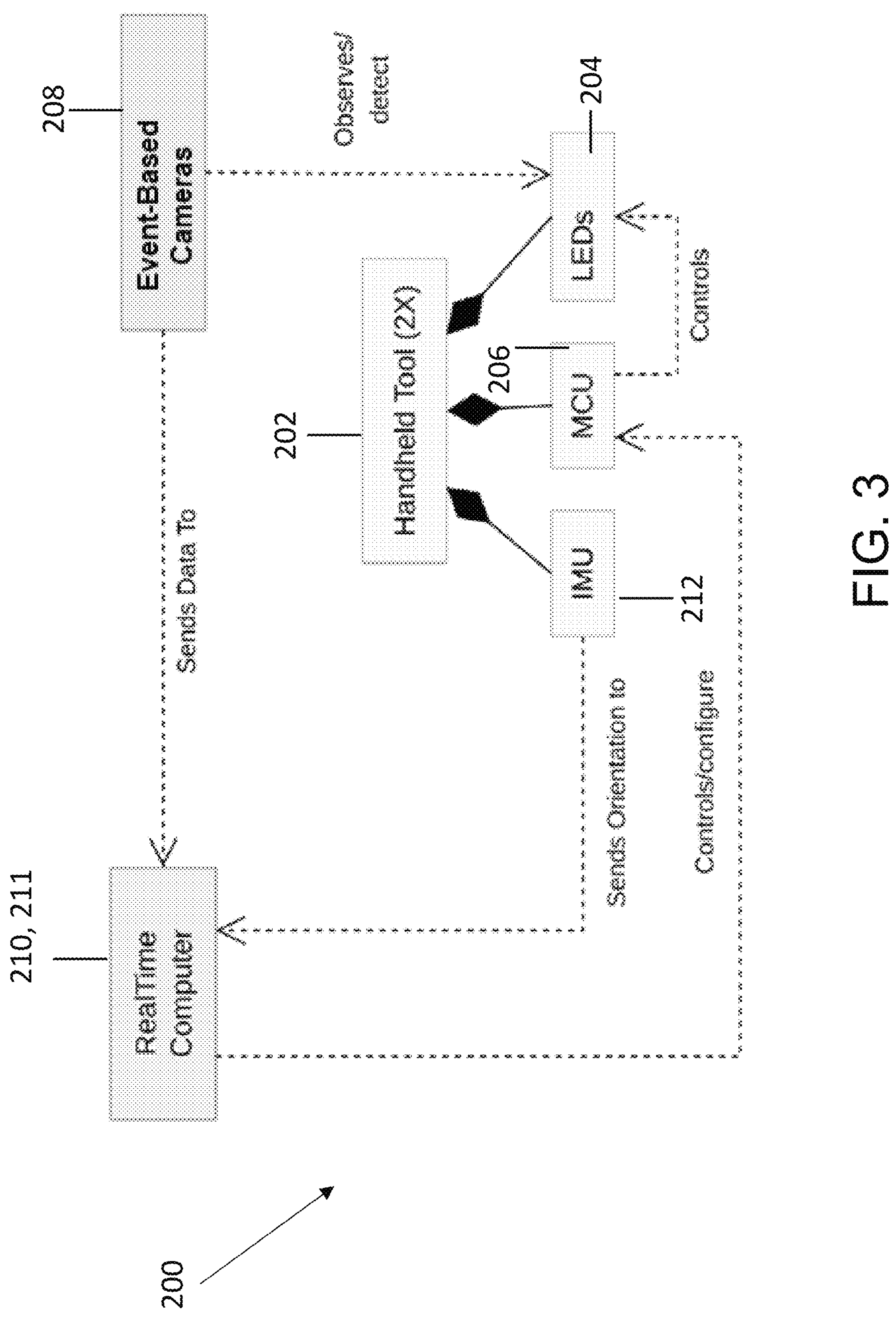
FIG. 3 is a hardware diagram schematically depicting the surgeon input tool tracking system.

The adapter assembly 110 (which will also be referred to as the "adapter") may include an enclosed or partially enclosed structure such as a housing or box, or it may be a frame or plate. The exemplary adapter 110 shown in the drawings includes mechanical input actuators 112 exposed to the exterior of the surgical instrument 102. In FIG. 3, two mechanical input actuators 112 are exposed at a first lateral face of the adapter 110. A second two mechanical input actuators 112 (not visible in FIG. 3) may be exposed at the second, opposite, lateral face of the adapter 110, preferably but optionally in a configuration identical or similar to the configuration shown in FIG. 3.

Each of the mechanical input actuators 112 is moveable relative to the adapter 110 between first and second positions. In the specific configuration shown in the drawings, the actuators are longitudinally moveable relative to the housing between a first (more distal) position and a second (more proximal) position such as that shown in FIG. 3. The direction of motion, however, is not required to be longitudinal and can extend in any direction.

In this configuration, the adapter thus has four drive inputs, one for each of the input actuators 112, exposed to its exterior. The illustrated adapter has two parallel planar faces, with two of these inputs positioned on each of the faces. While it may be preferred to include the inputs on opposite sides of the proximal body, other arrangements of inputs on multiple faces of the proximal body can instead be used. Each of these configurations advantageously arranges the drive inputs to maximize the distance between control inputs, minimizing stresses in the sterile drape that, in use, is positioned between the proximal body and the receiver 104. Co-pending US 2021/169595 includes further description of the adapter shown in FIG. 2.

The IDS 104 at the end of each manipulator 10 has an open position (shown in FIG. 2) in which it removably receives the adapter 110 of a corresponding instrument 12, to form an assembly 100. After the adapter 110 is placed within the IDS, the IDS is moved to the closed position shown in FIG. 1, capturing the adapter 110. In this position, the drive inputs 112 of the adapter can engage with corresponding drive outputs 114 of the IDS. As described in detail in co-pending US 2021/169595, user input at the input devices 16, 18 commanding jaw open-close, pitch or yaw articulation etc. of the instrument causes electromechanical actuators in the IDS to move the drive outputs 114. The motion of those drive outputs moves corresponding ones of the adapter's drive inputs 112, altering tension on the instrument's drive cables in a manner that causes the desired motion at the instrument's end effector.

As discussed, manipulation of the input devices 16, 18 results in signals that are processed by the system to generate instructions for commanding motion of the manipulators in order to move the instruments in multiple degrees of freedom including pitch and yaw of the instrument shaft relative to a remote center of motion (RCM) aligned with the incision site, roll of the shaft relative to the longitudinal axis of the instrument shaft, and movement of the instrument along its longitudinal axis. Input from the user input may further be used to control operation of electromechanical actuators/motors (such as those in the IDS described above) that drive instrument functions such as articulation, bending, and/or actuation of the instrument end effectors. One or more control units 30 are operationally connected to the robotic arms and to the user interface. The control units receive user input that is generated as a result of movement of the input devices and that corresponds to the movement of the surgical instruments desired by the user. It uses that user input to generate commands for the robotic arms to manipulate the surgical instruments so that the surgical instruments are positioned and oriented in accordance with the input provided by the user.

Surgeon Input System

FIG. 3 schematically illustrates a surgeon input system 200 used to generate user input. System 200 includes at least two surgeon input tools 202 (also referred to herein as "tools") that are held by a user. Each tool includes a plurality of active tracking elements (preferably LEDs) 204 and a controller 206 for controlling operation of the LEDs. In preferred embodiments, the controllers are microcontrollers mounted within each tool 202. The tools 202 are intended to be operated at a surgeon console, where the surgeon may manipulate the tools 202 while observing a display (see display 20 in FIG. 1) showing images captured by the endoscope/laparoscope placed in the patient's body.

Figure 4:
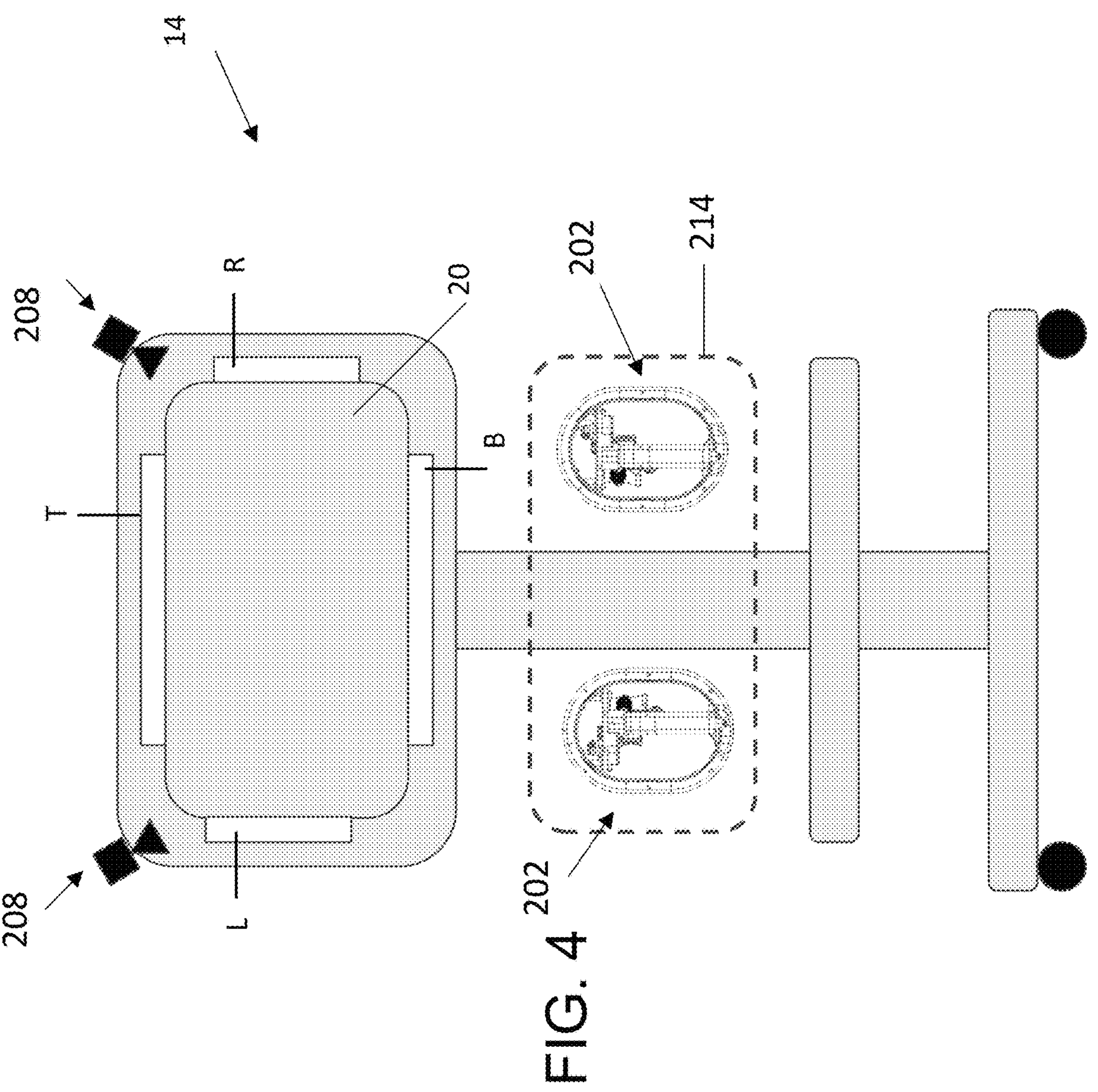
FIG. 4 is a front elevation view of an exemplary surgeon console employing the disclosed tracking system and employing a workplace management scheme configured to alert a user when tools are moved outside the defined tool tracking volume.
Figure 5:
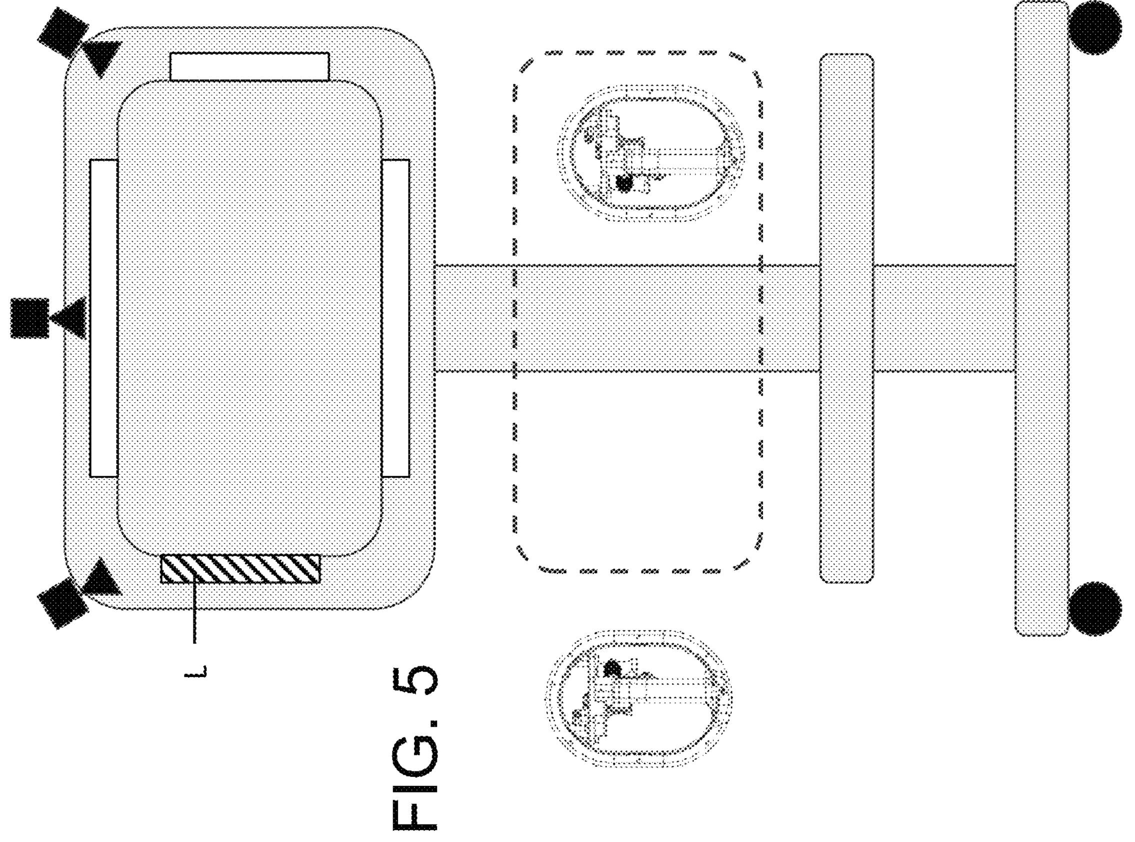
FIGS. 5 and 6 are similar to FIG. 4 and show alerts being displayed. These figures also show alternatives to the camera numbers and positions shown in FIG. 4.
Figure 6:
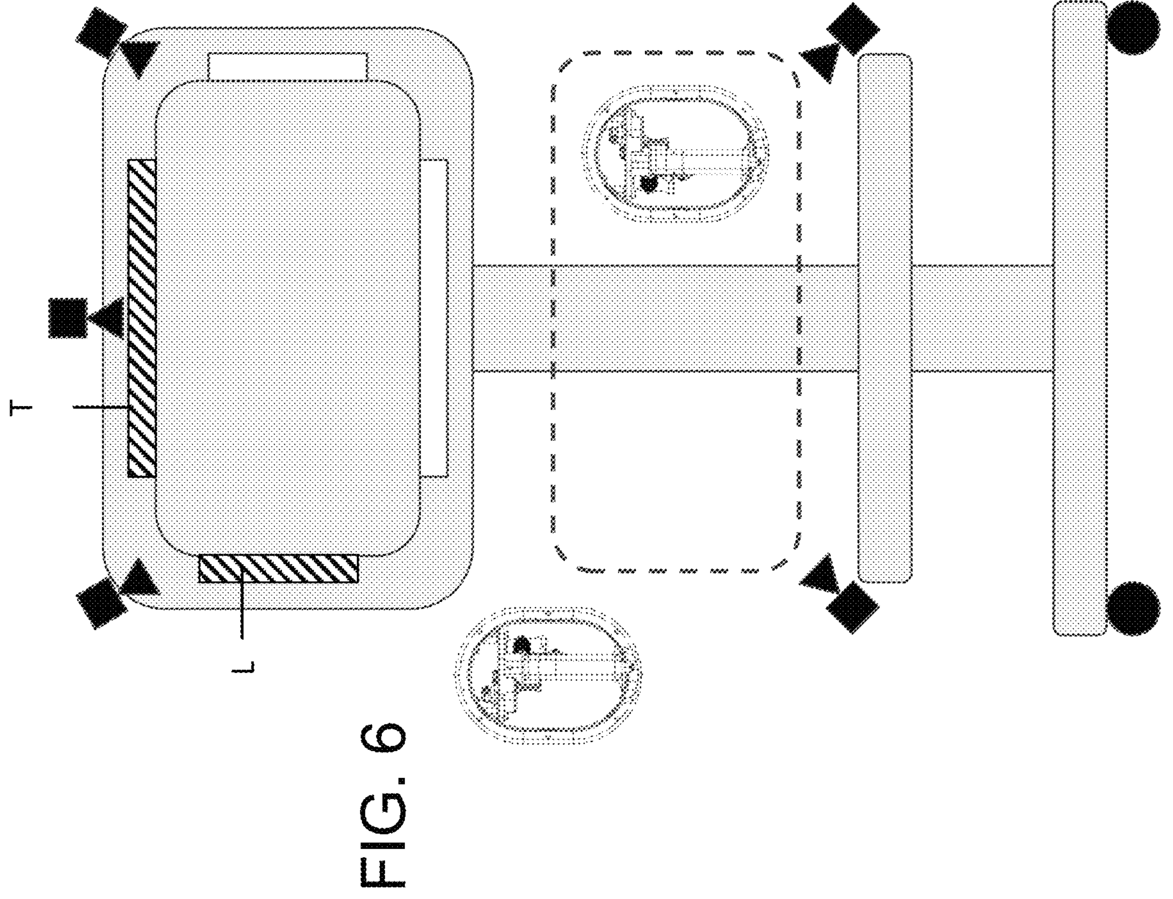

Two, three, or more event-based cameras 208 are positioned such that typical movement of the tools 202 during a surgical procedure is within a trackable tool motion volume at the console. The trackable tool motion volume may be defined as the region of overlap between the fields of view of the event-based cameras 208. A two-camera configuration is shown in FIG. 4. FIG. 5 illustrates the use of three cameras above the display. FIG. 6 shows an additional two cameras below the display. The cameras are mounted at fixed positions at the console, so their positions relative to the surgeon's workspace is known.

Modified systems might use a single event-based camera. In such systems, the trackable tool motion volume may be defined as the field of view of the single event-based camera.

Each tool may additionally, but optionally, include an inertial tracking component such as an IMU 212, accelerometer, gyroscope, etc. The IMU sensors produce regularly cadenced measurements of 6 or 9 axes of data, including linear acceleration, angular velocity, and referenced orientation.

Computer 210 is in communication with the event-based cameras 208 and the MCUs 206. The computer includes a memory 211 storing instructions executable to perform the tool tracking functions described elsewhere in this application. The computer 210 may be part of the computer 30 described in connection with FIG. 1, or it may be a separate computer in communication with the computer 30. In use, computer 210 processes data from the event-based cameras 208 and the IMUs 212 (if used) to calculate the poses (position and orientation) of each tool in six degrees of freedom (DOF). It should be mentioned that although FIG. 3 shows the IMU sending data directly to the computer, the data may alternatively be transmitted to the computer via the MCU.

Event-Based Camera Features

Cameras 208 employ event-based sensors, also known as dynamic vision sensors (DVS), which are image sensors that operate differently than traditional camera sensors. Non-limiting examples of event-based cameras that may be used with the system are those sold by Prophesee, which uses the Sony IMX 636/637 Stacked Event-Based Vision Sensor. In a conventional camera, the light intensity of each pixel across the entire image sensor is captured at a known interval (typically using a mechanical or electronic shutter), called the frame rate. Rather than capturing entire frames of images (where each frame captures data from all pixels), an event-based sensor detects and reports only changes in pixel-level brightness. Because they are not limited by a frame rate, use of event cameras in the disclosed system allows movement of the input tools to be tracked at a much faster rate than is possible using conventional cameras, including those currently used for medical device tracking.

Each pixel of the DVS sensor operates independently and asynchronously, reporting changes in brightness (both positive and negative) as they occur. When these changes, referred to as "events," are detected, they are reported with a timestamp and the spatial (x, y) coordinates of the pixel where the change occurred. When there is no change in brightness at a pixel, no event is reported for that pixel. As LEDs on the tool move across the field of view of the sensors 208, only the pixels affected by the motion will generate events. This allows the event-based cameras to operate with extremely low latency, with event detection and transmission occurring in microseconds.

Event cameras used in the disclosed system may be provided with filters that limit the wavelengths of light that can reach the camera sensors. For example, each event camera may be equipped with a filter that allows light in the infrared range of the electromagnetic spectrum to pass through, but that blocks light in the visible range (and, optionally, that blocks light in the ultraviolet range). In one embodiment, each event camera is equipped with an infrared pass filter.

LED Features

Turning now to operation and features of the LEDs, preferred embodiments use multiple LEDs per surgeon input tool. In preferred embodiments, at least 8 LEDs are positioned on each tool. One exemplary embodiment uses 18 LEDs per handle, but other numbers of LEDs can be used.

The LEDs are preferably infrared LEDs, i.e. LEDs producing electromagnetic radiation in the infrared band (700 nm to 1 mm) of the electromagnetic radiation spectrum. Preferred LEDs have a wide viewing angle. In some embodiments, this viewing angle may be 90 degrees or higher, 100 degrees or higher or, most preferably, 150 degrees or higher. In contrast, LEDs used for infrared beaming applications, where infrared light is used to send signals to electronic devices (e.g. communication from a remote control to a television), typically have a viewing angle of around 30 degrees. A "viewing angle" of an IR LED may be defined with reference to the cone-shaped beam of infrared light that emanates from the LED and within which the intensity of the light is greater than or equal to 50% of the intensity of the light within the brightest part of the cone (typically the center). Said another way, the viewing angle is the angle at which the light's intensity falls to half of what it is at the center or the brightest point of the cone.

As discussed below, the plurality of LEDs are preferably mounted to a tracking frame (see, e.g., tracking frame 218 of FIGS. 7A and 7B). The LEDs on each tracking frame are spaced apart from neighboring LEDs by a defined minimum distance. In some embodiments, this minimum distance may be approximately 30 mm or higher, approximately 40 mm or higher, or approximately 50 mm or higher.

The MCU causes the LEDs to blink with a pulse-width modulated (PWM) signal so that each LED operates with a different combination of frequency (Hz) and duty cycle (percent) compared with the other LEDs The LEDs may be high dynamic range LEDs in some implementations.

Input from the event cameras is filtered such that the system considers only changes that occur at the specific frequencies at which the LEDs are caused to blink. The LED frequencies are chosen to be high in order to filter out movement of the surgeon and tool structure, which occurs at a much slower rate. Without limiting the scope of the invention, LEDs may be driven to blink at frequencies above 700 Hz, such as in a range of 700 Hz-1000 Hz or 700 Hz-1200 Hz, or at frequencies above 800 Hz, such as in a range of 800 Hz and 1000 Hz or 800 Hz-1200 Hz. As a result, the event cameras capture movement only of the relevant LEDs and do not capture surgeon movement or even movement of the tool structure. The LED blink frequency is preferably tuned to match the desired rate of detection by the event camera. Increasing blink frequency results in faster detection, while decreasing blink frequency results in slower detection.

Ideally, LEDs that are positioned adjacent to one another on the tracking frame will have significantly different frequencies. It is also preferred that the surgeon input tool to be held in the user's left hand have LEDs operating at different frequencies than the LEDs on the tool to be held in the user's right hand. The LEDs preferably blink at frequencies not perceptible to the human eye, so the flickering of the LEDs is not seen by the surgeon. Additionally, as discussed, infrared LEDs are preferred since much or all of their emitted light is beyond the visible spectrum.

The relative, fixed, positions of each LEDs (with its unique combination of frequency and duty cycle at which it is operated) with respect to its corresponding tool frame is known to the system.

In alternative embodiments, the algorithm may distinguish the LEDs using parameters other than frequency and duty cycle. Examples of other suitable parameters include shapes and colors.

Console and User Input Tool Features

FIG. 4 illustrates a console having a display 20. The event based cameras 208 are positioned to define a trackable tool motion volume 214 that is ergonomically convenient for the surgeon to operate within while observing the laparoscopic/endoscopic camera output on the display 20. As discussed, this volume is the region of overlap between the fields of view of the event-based cameras 208. Where three or more cameras are used, the volume may be defined as any region in which the fields of view of at least two of the event-based cameras 208 overlap.

The console may include feedback regions L, R, T, B at the left, right, top and bottom of the display, respectively. These regions are positioned so that the surgeon can see them using peripheral vision while observing the surgery on the display. These regions provide visual feedback alerting the user if a tool 202 has been moved outside the trackable tool motion volume 214. As one example, the relevant region may light up or change color if a tool has been moved outside of the trackable tool motion volume. In FIGS. 5 and 6, illumination of a region is represented by dashed lines. FIG. 5 shows an alert that the left tool has been moved to the left of the trackable tool motion volume. FIG. 6 shows an alert that the left tool has been moved to a position that is above and to the left of the trackable tool motion volume. The alerts may be generated as the user approaches a boundary of the trackable tool motion volume, or when the user has crossed that boundary. Where the tool has crossed the boundary, the system might simultaneously suspend operation of the robotic manipulator associated with that tool until the tool is brought back into the trackable tool motion volume and the user informs the system that tracking of that tool should be resumed. This workspace management configuration may be used with other forms of user input tracking schemes, including those using more traditional cameras, rolling shutter or global shutter cameras, or electromagnetic tracking.

Figures 7A, 7B:
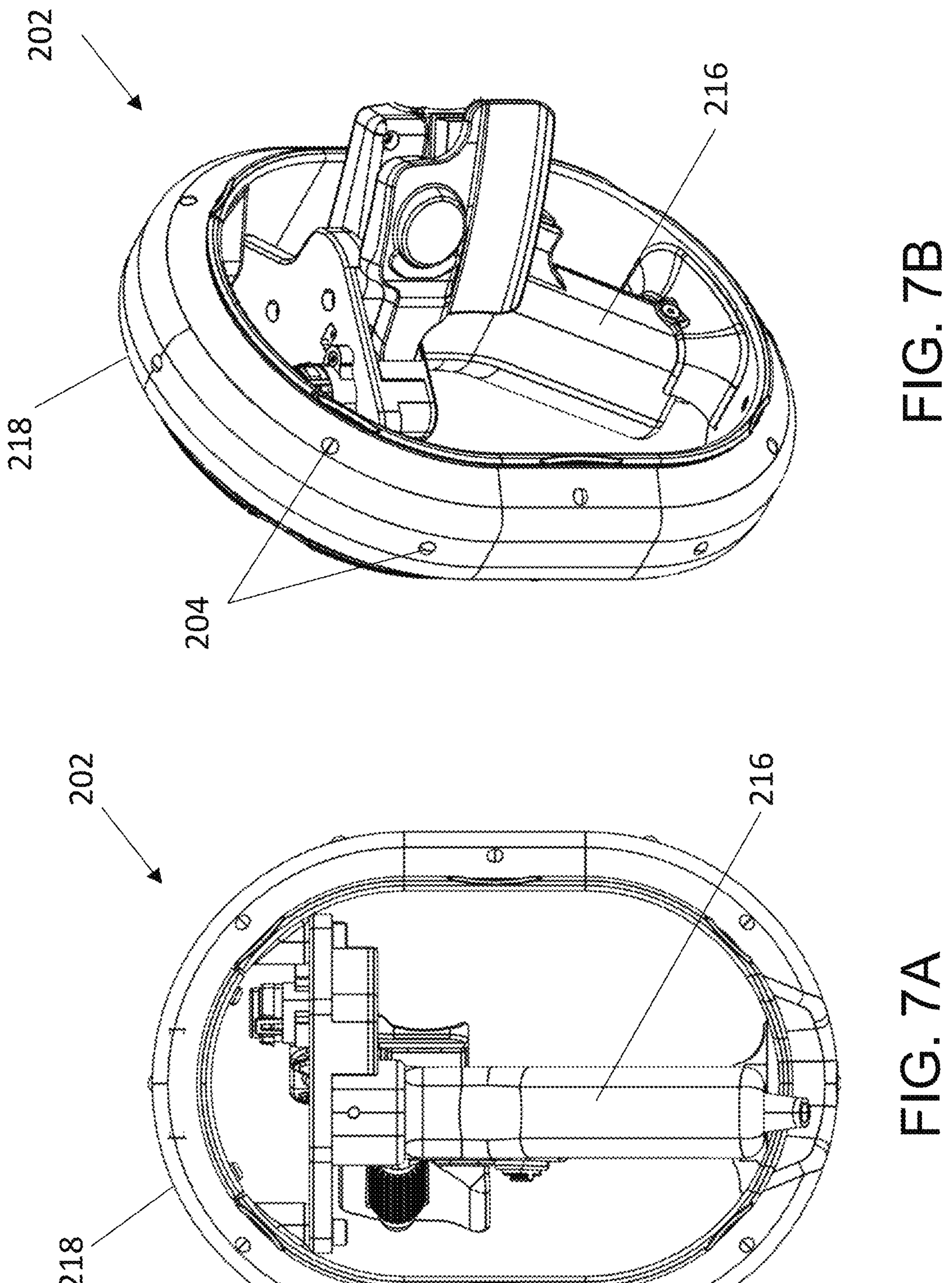
FIGS. 7A and 7B are a rear elevation view and a front perspective view, respectively, of an exemplary surgeon input tool.
Figure 8:
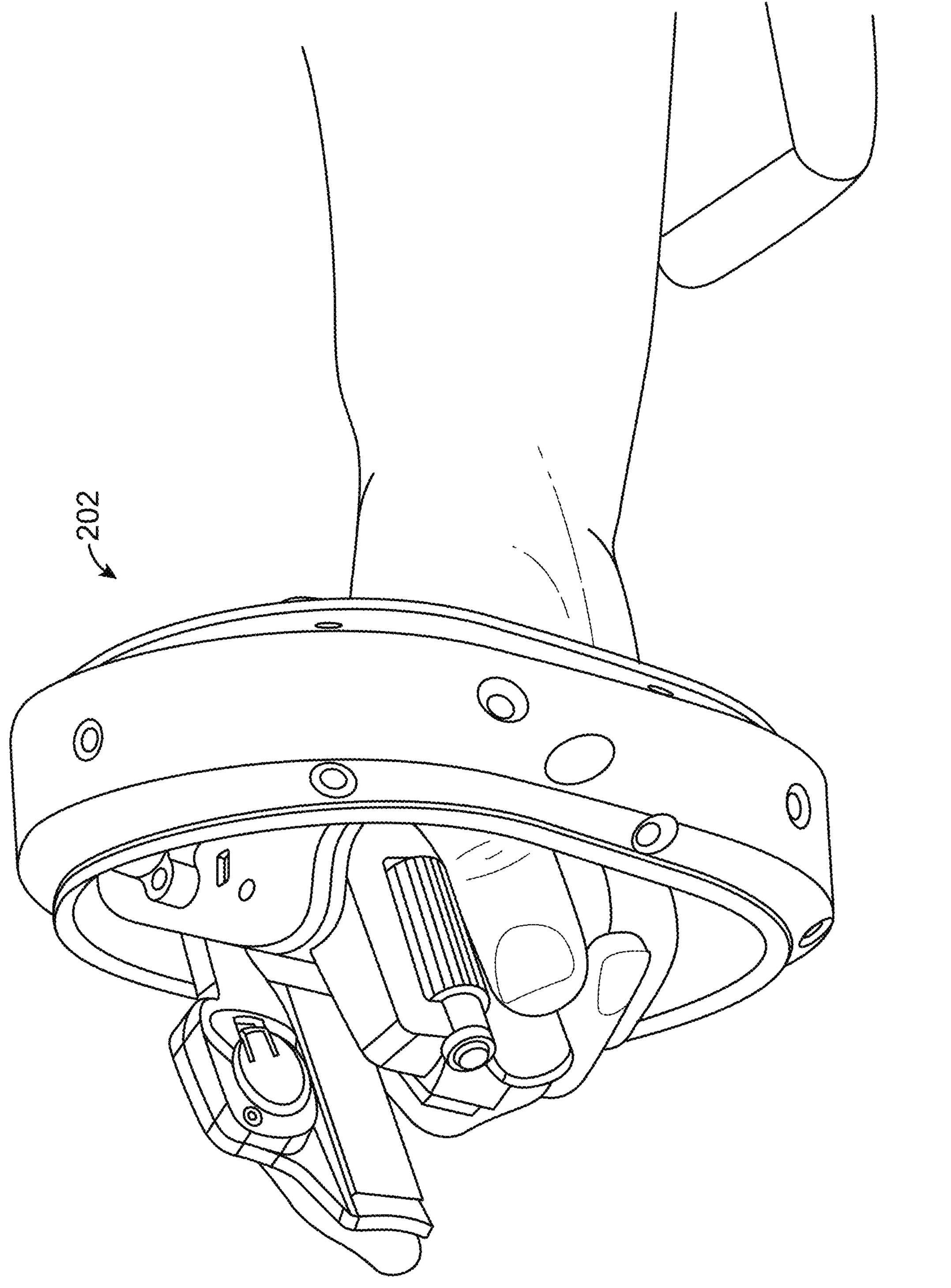
FIG. 8 illustrates the tool shown in FIGS. 7A and 7B being held by a user.
Figures 9A, 9B:
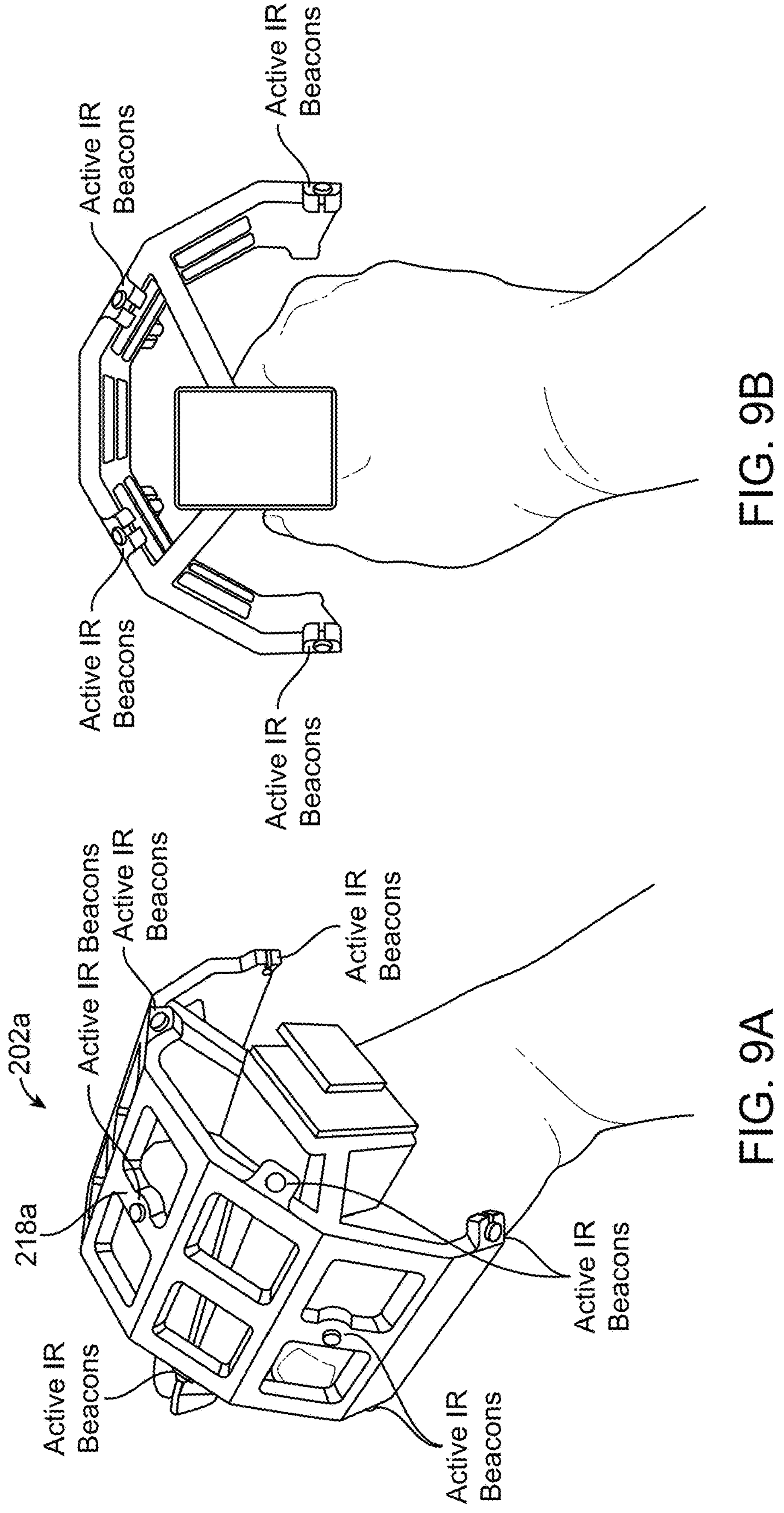
FIGS. 9A and 9B are a perspective view and a rear elevation view, respectively, showing a second embodiment of a surgeon input tool being held by a user.
Figure 10B:
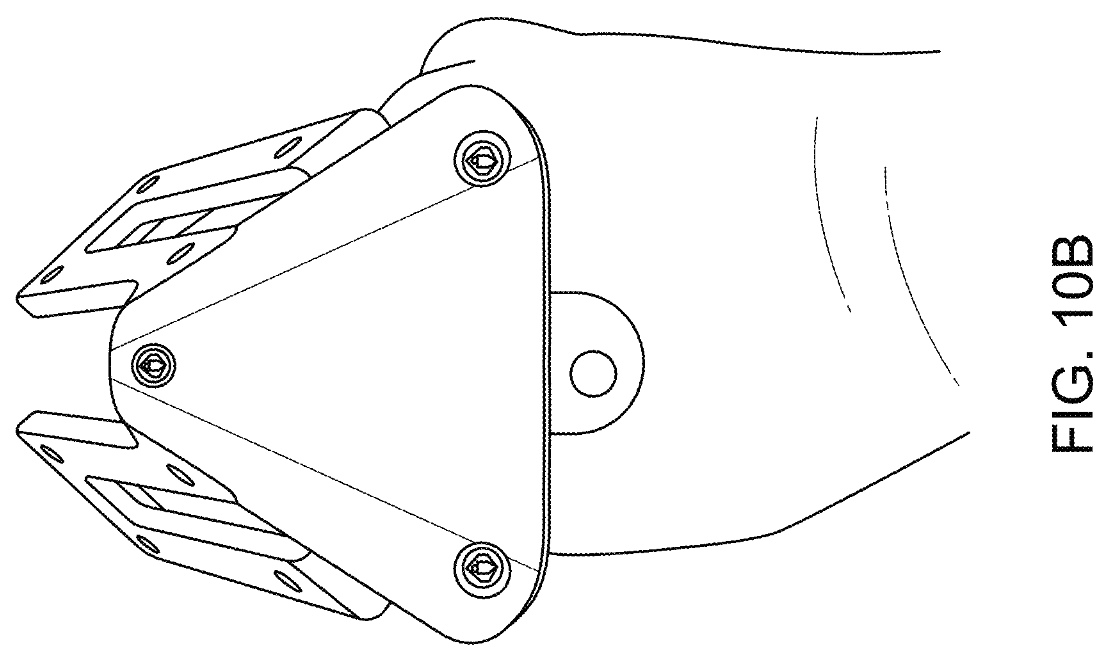
FIGS. 10A and 10B are a perspective view and a rear elevation view, respectively, showing a third embodiment of a surgeon input tool being held by a surgeon.
Figure 10A:
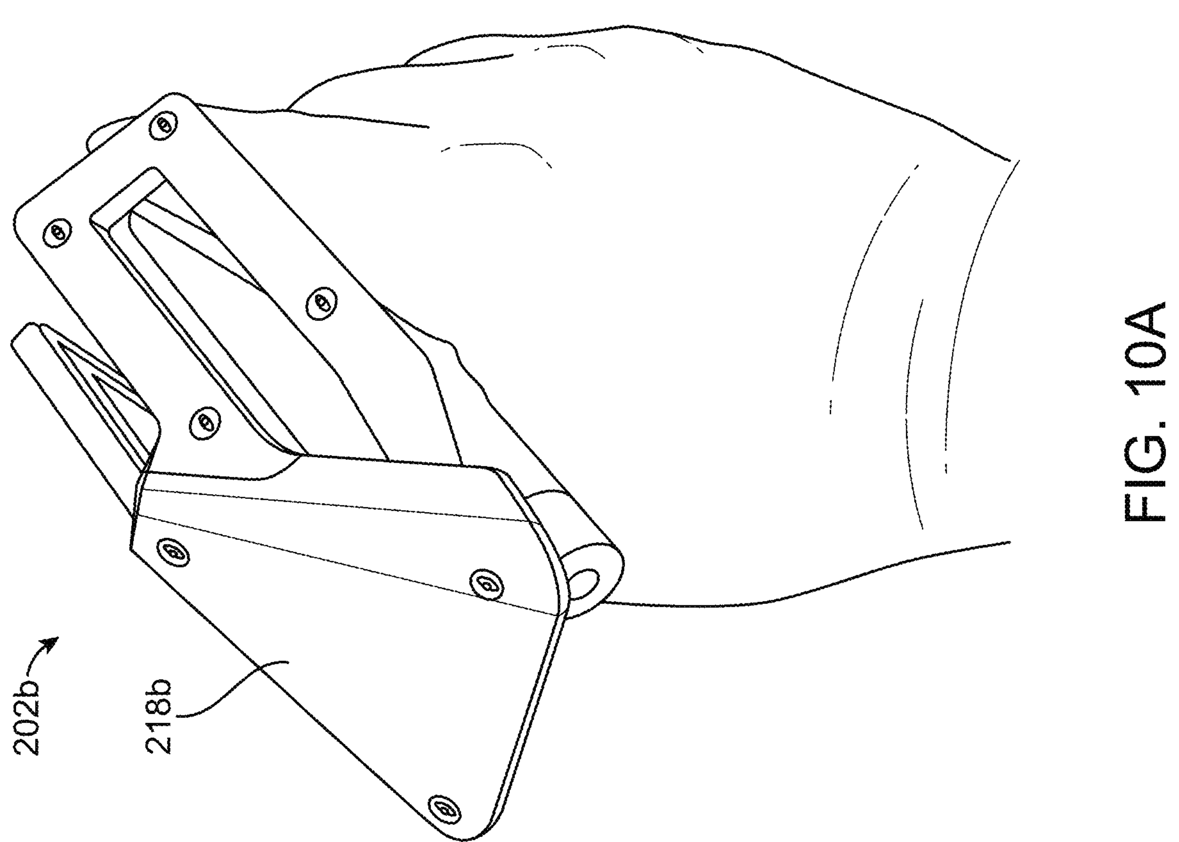

One example of a surgeon input tool 202 is shown in FIGS. 7A and 7B. Tool 202 includes a grip 216 grasped by a user and any combination of levers, scissor grips, pincers, joysticks, touchpads, roll knobs, etc. within reach of the user's fingers while s/he grasps the grip 216. For example, movement of levers or pincers would generate signals from encoders at the tool that are used to command opening and closing of the jaws of an instrument. The illustrated tool 202 preferably includes a tracking frame 218 on which the LEDs are positioned. FIGS. 7A, 7B, 8A and 8B illustrate two alternative tools 202*a*, 202*b*, respectively, each of which uses a tracking frame 218*a*, 218*b* having an alternative geometry. The tracking frames are configured so that LEDs are present on at least two but preferably three or more planes of the tool. This helps minimize the chance that a tool will be positioned in a way that none of its LEDs are within view of the event-based cameras. In other embodiments, in lieu of a tracking frame, the LEDs are located directly on the grip 216. As noted, the present invention is not limited to any particular tool or tracking frame design or configuration. Other embodiments may be hand-mounted rather than hand-held. Some handles may incorporate tactile (e.g., vibratory) motors and/or brushed/brushless DC motors for haptic feedback.

The tool is preferably one that is not mechanically unconstrained during use, although it may be tethered to the console by a cable providing electronic communication and power transmission. In alternative embodiments, the tool may be mounted to a structure that partially restricts its motion. This might be useful, for example, if the surgeon console allows the surgeon the ability to give user input using laparoscopic motion. In such cases, the tool might be mounted to a structure that requires motion of the tool to occur with respect to a pivot that simulates the fulcrum of a surgical instrument moving at an incision site.

Surgeon Input System Operation

Use of the system 200 to determine pose data for each of the tracked surgeon input tools 202 will next be described. In use, each of the tools 202 is paired with a select one of the robotic manipulators, so that movement of that tool 202 will result in corresponding movement of the surgical instrument paired with that manipulator. A surgeon positioned at the surgeon console, will move the tools, causing each tool to move in a way that replicates the desired motion of the surgical instrument within the surgical site. Tool movements may therefore include translational movement in x, y and z directions (side-side, up-down, and translation along the longitudinal axis of the instrument), as well as pitch, yaw, and axial roll (corresponding to roll of the surgical instrument about its longitudinal axis). The system 200 tracks the pose (position and orientation) of each tool in order to determine the movements of the tool. Tool movements are converted to velocities used by the robotic system controller to control motion of the surgical instrument through a combination of manipulator movement and, where applicable, articulation at the distal part of the instrument shaft through actuation of the IDS.

Each event-based camera 208 transmits a continuous stream of "events" representing increases or decreases in brightness detected by the camera sensor. The data corresponding to each event includes both (i) the X,Y position, in the image frame, at which the event occurred, and an identification of whether the brightness increased or decreased, and (ii) the exact timestamp marking the time at which the pixel brightness changed. In typical event-based sensors, the timestamp is generated with microsecond accuracy. The clocks of each camera 208 used in the system are synchronized, ensuring that each camera generates the same timestamp for a given event. One of the cameras can be configured to generate a sync signal used to ensure synchronization, or the computer can generate the sync signal.

In use, the event-based cameras function to track the positions of the LEDs while those LEDs are controlled by the microcontroller. As discussed, each LED blinks according to a combination of pulse-width modulated (PWM) frequency (Hz) and duty cycle (percent) that differs from the combination of those parameters used for the other LEDs. When an LED 204 blinks, the event-based camera sensors detect the turning-on and turning-off of the LED as a cluster of positive (on) or negative (off) events.

In the event-based camera data, a signal having positive polarity corresponds to the time when an LED was turned on, and a negative polarity corresponds to the time when the LED was turned off. Using those two timestamps, the system calculates both the PWM period and duty cycle, and from that data it can identify which of the LEDs on the tools is the subject of the corresponding event. Once a particular LED is identified, the system tracks that LED in each camera's image plane. More specifically, for each event camera, the data resulting from each identified LED is processed using a marker tracking software module to determine the 2D position (in that camera's image frame) at any given moment in time for each blinking LED within its view. As is well known to those skilled in computer vision, the 2D projected point in the coordinates of an image sensor is computed by transforming the 3D point in world coordinates into a 2D point in pixel coordinates on the camera's image plane.

The marker tracking software modules for the two (or three+) cameras are run in parallel. This results in output of the 2D positions of each visible LED in each camera's plane at a given point in time and results in tracking of each LED in each camera frame as subsequent events for that LED are reported by the camera sensors.

Using the 2D centroids of the determined positions of the identified markers, and the known positions of those markers on the user input tool geometry, the system calculates the 6 DOF pose of the surgeon input tool on which the LEDs are positioned. As is known to those skilled in the art, solving the pose estimation problem can be described as finding the post that minimizes the reprojection errors. This may be performed, for example, using methods described in G. Terzakis and M. Lourakis, A Consistently Fast and Globally Optimal Solution to the Perspective-n-Point Problem, http://www.ecva.net/papers/eccv_2020/papers_ECCV/papers/123460460.pdf, which is incorporated herein by reference, or using other pose-estimation techniques known to those skilled in the art. The estimated pose is continuously calculated for each surgeon input tool, and used by the robotic controller to control motion of the corresponding surgical instrument. If the surgeon input tool uses an IMU, the system receives angular velocity and linear acceleration data from the IMU and applies a Kalman filter to the IMU data and the pose estimated using the image sensor to determine the final estimated pose used by the robotic controller. IMU data may also be used to trigger suspension of operation of the robotic manipulator paired with the tool in which the IMU is located if there is a sudden spike in the values reported by the IMU, such as would result from fast and sudden motion of a user input tool, from the dropping of the tool or from collisions with a hard object, such as the other control handle, an arm rest, or the other components of the console. In embodiments that do not use IMUs, this suspension in activity can instead be triggered when velocity or acceleration of a tracked LED exceeds a predetermined threshold.

It will be understood by those skilled in the art that the steps of calculating the 2D projection of an LED on a sensors image plane, and estimating the 3D pose information of the tool require that the algorithms take into account the intrinsic parameters of each event-based camera sensor. To ensure accuracy in tracking and pose estimating, calibration of the camera sensors is performed. Calibration may be performed by positioning a target with LEDs in a known pattern blinking at known frequencies. The calibrations of the cameras may be periodically checked by users of the system by moving a static pattern in front of the cameras. Calibration techniques for image sensors are known to those skilled in the art and will not be detailed here.

Where more than two cameras are used, algorithms may be employed to switch between which event-based camera is currently being used as an input source or as the primary input source. This may be conducted if, for example, the user input tool is reaching the periphery of the tracked visible space for a particular camera.

ALTERNATIVE EMBODIMENTS

As described above, preferred implementations of the system track the user input tool using event camera data alone or in combination with inertial tracking data from the IMU. Alternative embodiments may combine multiple forms of tool tracking in alternative ways. As one example, inertial tracking using data from the IMU can be used to determine relative or dynamic pose information, and the event based cameras used only for position calculations, such as (absolute) positional information at startup, and/or periodic redundancy on absolute position during use. In such an embodiment, only one event-based camera need be used, although multiple such cameras would also be useful for minimizing occlusions and dead zones within the active tracked region. Other embodiments might combine the event-based tracking features of the described inventions with other tracking modalities, such as electromagnetic tracking.

While certain embodiments have been described above, it should be understood that these embodiments are presented by way of example, and not limitation. It will be apparent to persons skilled in the relevant art that various changes in form and detail may be made therein without departing from the scope of the invention characterized by the claims. This is especially true in light of technology and terms within the relevant art(s) that may be later developed. Moreover, features of the various disclosed embodiments may be combined in various ways to produce various additional embodiments.

All patents, patent applications and printed publications referred to above, including for purposes of priority, are incorporated herein by reference.

The invention claimed is:

1. A user input system for providing provide input to a robotic surgical system for use in commanding motion of the robotic manipulator, the user input system comprising:

a surgeon input tool configured to be worn or held by a user, the surgeon input tool including a plurality of LEDs, each LED configured to emit light, wherein each LED on the surgeon input tool is configured to blink with a combination of blink frequency and duty cycle that differs from the combination of blink frequency and duty cycle of any other LED on the surgeon input tool;

at least one event-based camera sensor disposed around a surgeon console;

at least one processor having a memory, the memory storing instructions executable by the processor to:

receive input in response to sensing of light from the LEDs by the event-based camera sensor; and in response to the received input, generate motion commands corresponding to desired movement of the surgical instrument by the robotic manipulator arm.

2. The system of claim 1, wherein the surgeon input tool is configured such that each LED in the plurality of LEDs blinks at a blink frequency, wherein the blink frequency of each LED differs from the blink frequency of the other LEDs.

3. The system of claim 1, wherein the instructions are executable by the processor to, based on the received input, determine a position of the surgeon input tool.

4. The system of claim 1, wherein the instructions are executable by the processor to, based on the received input, determine a pose of the surgeon input tool.

5. The system of claim 1, wherein each LED blinks at a blink frequency of at least 700 Hz.

6. The system of claim 5, wherein each LED blinks at a blink frequency in a range of 700 Hz-1200 Hz.

7. The system of claim 1, wherein the system includes at least two event-based camera sensors.

8. The system of claim 1, wherein each LED emits light in the infrared range of the electromagnetic spectrum.

9. The system of claim 1, further including an inertial sensor carried by the surgeon input tool.

10. A method for providing provide input to a robotic surgical system, comprising:

causing a plurality of LEDs on a surgeon input tool to emit light, including causing each LED in the plurality of LEDs to blink with a combination of blink frequency and duty cycle that is different than the combination of blink frequency and duty cycle of the other LEDs in the plurality of LEDs;

manually moving the surgeon input tool;

sensing light emitted from the plurality of LEDs using at least one event-based camera sensor;

receive input in response to sensing of the light by the event-based camera sensor; and in response to the received input, generate motion commands corresponding to desired movement of a surgical instrument by a robotic manipulator arm.

11. The method of claim 10, wherein causing the plurality of LEDs to emit light includes causing each LED in the plurality of LEDs to blink at a blink frequency that is different than the blink frequency of the other LEDs in the plurality of LEDs.

12. The method of claim 10, wherein the method includes, based on the received input, determining a position of the surgeon input tool.

13. The method of claim 10, wherein the method includes, based on the received input, determining a pose of the surgeon input tool.

14. The method of claim 10, wherein causing the plurality of LEDs to emit light includes causing each LED in the plurality of LEDs to blink at a blink frequency of at least 700 Hz.

15. The method of claim 14, wherein causing the plurality of LEDs to emit light includes causing each LED in the plurality of LEDs to blink at a blink frequency in a range of 700 Hz-1200 Hz.

16. The method of claim 10, wherein causing the plurality of LEDs to emit light includes causing each LED to emit light in the infrared range of the electromagnetic spectrum.

17. The method of claim 16, wherein causing the plurality of LEDs to emit light includes causing each LED to emit light with a viewing angle of at least 150 degrees.

18. A method for providing provide input to a robotic surgical system, comprising:

causing a plurality of LEDs on a surgeon input tool to emit light, including causing each LED in the plurality of LEDs to blink at a blink frequency of at least 700 Hz;

manually moving the surgeon input tool;

sensing light emitted from the plurality of LEDs using at least one event-based camera sensor;

receive input in response to sensing of the light by the event-based camera sensor; and in response to the received input, generate motion commands corresponding to desired movement of a surgical instrument by a robotic manipulator arm.

19. The method of claim 18, wherein causing causing each LED in the plurality of LEDs to blink at a blink frequency of at least 700 Hz includes causing each LED in the plurality of LEDs to blink at a blink frequency in a range of 700 Hz-1200 Hz.

20. The method of claim 18, wherein the surgeon input tool further includes an inertial tracking sensor, and wherein the method includes generating the motion commands in response to the received input and input from the inertial tracking sensor.

* * * * *